(12) United States Patent
Nylund

(10) Patent No.: US 7,858,100 B2
(45) Date of Patent: Dec. 28, 2010

(54) BACTERIUM AND VACCINE

(75) Inventor: Are Nylund, Bønes (NO)

(73) Assignee: Intervet International B.V., Boxmeer (NL)

( * ) Notice: Subject to any disclaimer, the term of this patent is extended or adjusted under 35 U.S.C. 154(b) by 81 days.

(21) Appl. No.: 12/093,075

(22) PCT Filed: Nov. 9, 2006

(86) PCT No.: PCT/EP2006/068292

§ 371 (c)(1),
(2), (4) Date: May 8, 2008

(87) PCT Pub. No.: WO2007/054537

PCT Pub. Date: May 18, 2007

(65) Prior Publication Data

US 2009/0220525 A1    Sep. 3, 2009

(30) Foreign Application Priority Data

Nov. 10, 2005   (EP) ................... 05110602

(51) Int. Cl.
| | |
|---|---|
| A61K 39/02 | (2006.01) |
| A61K 39/40 | (2006.01) |
| C12Q 1/68 | (2006.01) |
| C07H 21/00 | (2006.01) |

(52) U.S. Cl. .............. 424/234.1; 424/164.1; 424/184.1; 424/201.1; 424/203.1; 435/6; 435/252.1; 536/23.1; 536/24.33

(58) Field of Classification Search ............... None
See application file for complete search history.

(56) References Cited

U.S. PATENT DOCUMENTS 7,550,145 B2 *   6/2009   O'Hagan et al. ......... 424/184.1

OTHER PUBLICATIONS

Santha et al Proceedings of the Symposium on Coastal Aquaculture Held At Cochin From Jan. 12-18, 1980 (Abstract).*
Mukherjee et al ICAR/CIFA. Bhubaneswar (India). Meeting Info. Natl. Symp. on New Horizons in Freshwater Aquaculture. Bhubaneswar (India). Jan. 23-25, 1991 (Abstract).*
Accession No. AY928394 , Nov. 8, 2005.*
C.Y. Hsieh, et al. Aquaculture, 254:129-138, (2006).
Database EMBL [online], EMBL Accession No. AY928394, Nov. 8, 2005.
P. Larsson, et al. Nature Genetics, 37:2, pp. 153-159, (2005).
S.-C. Chen, et al. Journal of Fish Diseases, 17:591-598, (1994).
M. Forsman, et al. International Journal of Systematic Bacteriology, 44:1, pp. 38-46 (1994).
A. Nylund, et al. Archives of Microbiology, 185:383-392 (2006).
Database EMBL [Online], EMBL Accession No. DQ309246, May 28, 2006.
A.B. Olsen, et al. Journal of Fish Diseases, 29:307-311 (2006).
Database EMBL [Online], EMBL Accession No. DQ295795, Apr. 1, 2006.

* cited by examiner

Primary Examiner—Robert B Mondesi
Assistant Examiner—Padma V Baskar
(74) Attorney, Agent, or Firm—William M. Blackstone; Aaron L. Schwartz

(57) ABSTRACT

The present invention relates to a novel rod-shaped pleiomorphic non-motile Gram-negative bacterium causing a new, deadly, disease in fish, to a microbiological culture comprising said bacterium, to a vaccine comprising said bacterium and methods for the preparation of such a vaccine, to antibodies reactive with said bacterium, to diagnostic test kits and to the use of said bacterium.

10 Claims, 9 Drawing Sheets

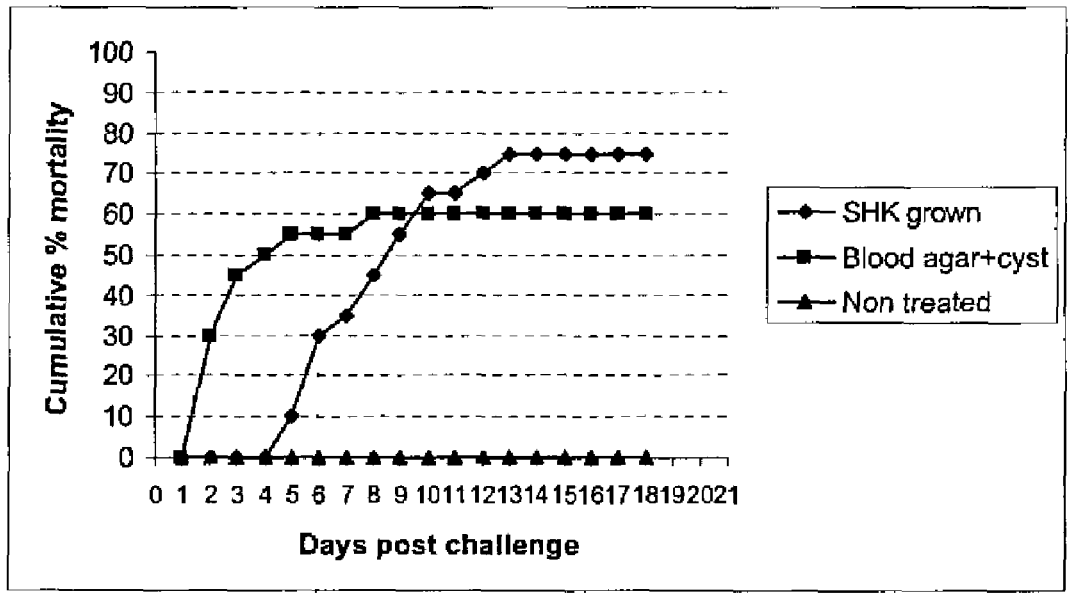
Figure 6 (cod)
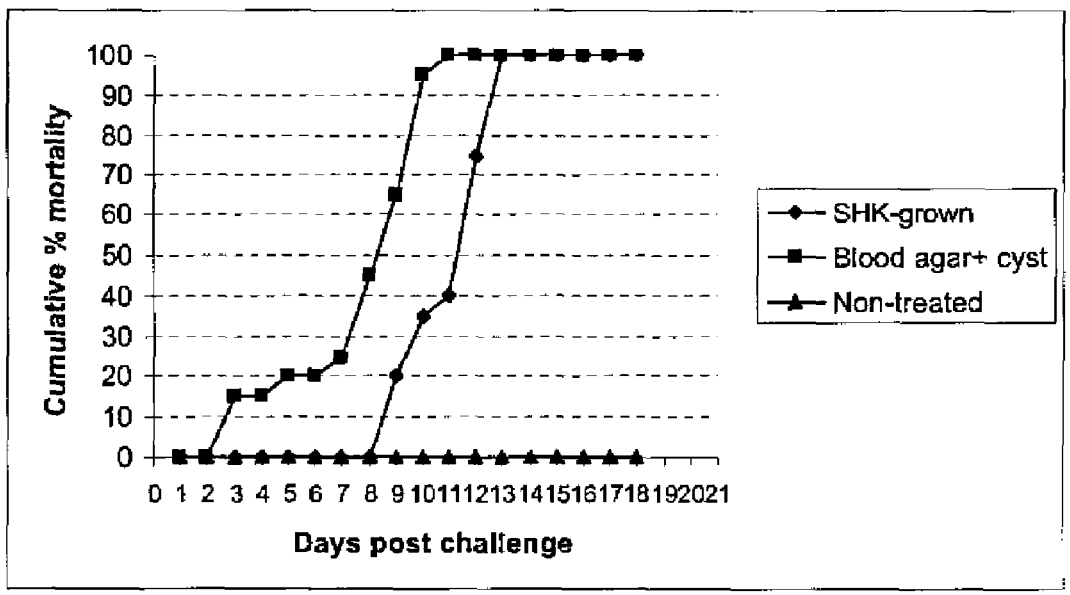
Figure 7 (salmon)

SEQUENCE LISTING

<160> NUMBER OF SEQ ID NOS: 9

<210> SEQ ID NO 1
<211> LENGTH: 1457
<212> TYPE: DNA
<213> ORGANISM: Francisella nsp.

<400> SEQUENCE: 1

```
taacaggtct tcggatgctg acgagtggcg gacgggtgag taacgcgtag gaatctgccc     60
atctgtgggg gataccagtt ggaaacgact gttaataccg cataatatct gcggattaaa    120
ggtggccttt gtgctgccgc agatggatga gcctgcgttg gattagctag ttggtagggt    180
aagggcctac caaggctacg atccatagct gatttgagag gatgatcagc cacattggga    240
ctgagacacg gcccaaactc ctacgggagg cagcagtggg gaatattgga caatggggga    300
aaccctgatc cagcaatgcc atgtgtgtga agaaggctct agggttgtaa agcactttag    360
ttggggagga aagcctataa gttaatagct tgtaggaagg acgttaccca aagaataagg    420
accggctaac tccgtgccag cagccgcggt aatacggggg gtccgagcgt taatcggaat    480
tactgggcgt aaagggtctg taggtggttt gttaagtcag atgtgaaagc ccagggctca    540
accttggaac tgcatttgat actggcaaac tagagtatgg tagaggaatg gggaatttct    600
ggtgtagcgg tgaaatgcgt agagatcaga aggaacacca atggcgaagg caacattctg    660
gatcaatact gacactgagg gacgaaagcg tggggatcaa acaggattag ataccctggt    720
agtccacgct gtaaacgatg agtactagct gttggattcg gtgtaaagga tctagtggcg    780
cagctaacgc gttaagtact ccgcctgggg actacggccg caaggctaaa actcaaagga    840
attgacgggg acccgcacaa gcggtggagc atgtggttta attcgatgca acgcgaagaa    900
ccttacctgg tcttgacatc ctgcgaactt tctagagata gattggtgcc ttcgggaacg    960
cagtgacagg tgctgcacgg ctgtcgtcag ctcgtgttgt gaaatgttgg gttaagtccc   1020
gcaacgagcg caacccctat tgatagttac catcattaag ttgggtactc tattgagact   1080
gccgctgaca aggcggagga aggtggggac gacgtcaagt catcatggcc ctacgaccag   1140
ggctacacac gtgctacaat gggtattaca gagggctgcg aaggtgcgag ctggagcgaa   1200
actcagaaag gtactcttag tccggattgc agtctgcaac tcgactgcat gaagtcggaa   1260
tcgctagtaa tcgcaggtca gaatactgcg gtgaatacgt tcccgggtct tgtacacacc   1320
gcccgtcaca ccatgggagt gggttgctcc agaagtagat agtttaacga atgggcgttt   1380
accacggagt gattcatgac tggggtgaag tcgtaacaag gtagccgtag gggaacctgc   1440
ggctggatca cctcctt                                                  1457
```

<210> SEQ ID NO 2
<211> LENGTH: 328
<212> TYPE: DNA
<213> ORGANISM: Francisella nsp.

<400> SEQUENCE: 2

```
aacggaaata cgaaaaaata gaaataagct ctaattacat attcaagtga tttagcatgg     60
tgtttgtaga taatatattt tagtgtaaat agaatgcggg tctgtagctc agttggttag    120
agcgcacccc tgataagggt gaggtcggta gttcgagtct actcagaccc accagtaatt    180
ttggggccat agctcaactg ggagagcacc tgctttgcac gtagggggtt agcggttcga    240
```

```
tcccgcttgg ctccaccata tttatttaca cgaagataga gatatttaac aatttagtat    300
agaaatagac ttaagtaaat aagtgcaa                                       328

<210> SEQ ID NO 3
<211> LENGTH: 1978
<212> TYPE: DNA
<213> ORGANISM: Francisella nsp.

<400> SEQUENCE: 3
gcggtagatg ccttggcatt cagaggcgat gaaggacgtg ttaatctgcg ataagcttcg     60
gggagctggt aaataagctt tgatccggag atttccgaat gggggaaccc acctaacaca   120
agttaggtac tcactcgaca tagagtgtag agcgaacgag gggaactgaa acatctaagt   180
acccttagga agagaaatca attgagattc ccatagtagt ggcgagcgaa gtgggaagag   240
cctggtgtga tttagctgta attatagtag aacaagttgg gaagcttgac gatagagggt   300
gatagtcccg tatacgaaat aattacagtg gaactaagca tgcgaacaag taggacgggg   360
cacgtgaaac cttgtctgaa tatgggggga ccatcctcca aggctaaata ctcctgaatg   420
accgatagtg aactagtacc gtgagggaaa ggtgaaaaga acccttataa agggagtgaa   480
atagaatctg aaaccgcttg catacaagca gtaggagcat tatttagtaa tgtgactgcg   540 tacctttttgt ataatgggtc agcgagttac ttttagtggc gaggataact gaataaggga   600
tccgtagcga aagcgagttt taataggcg ataagtcgct aggagtagac ccgaaaccgg   660
cgcgatctat ccatggccag gttgaaggtt gggtaatacc aactggagga ccgaacccaa   720
tactgttgca aaagtatggg atgagctgtg gatcggagtg aaggctaatc aagcacggag   780
atagctggtt ctcctcgaaa actatttagg tagtgcctcg tgtataactc attggggtaa   840
agcactgttt cgacaatggg ggttttacga ccttactgac tcgatgcaaa ctcagaatac   900
gatgaagttc aatcacggga gacacactgc gggtgctaag gtccgtagtg aaagggaaa   960 cagcccagac cgccaactaa ggtccccaag tcatagctaa gtgggaaacg aagtgggaag  1020
gcccagacag ccaggaggtt ggcttagaag cagccaccct ttaaagaaag cgtaatagct  1080
cactggtcga gtcggcctgc acgtaagatt taacgggggct aagctatgca ccgaagttgt  1140
ggaatatatt tagtatattg gtaggggagc gttctgtaag ccgatgaagg tgtgttgaga  1200
agcatgctgg aggtatcaga agtgcgaatg ctgacatgag taacgtaaaa taagtgagat  1260
tcttattggc cgaaaaccca aggattccta cgcaatgtta atcaacgtag ggtaagccgg  1320
cccctaaggc gtagctgaag agtgaagtcg atgggaaaca ggttaatatt cctgtgccgc  1380
ttatatgaac gaaggaggga cggagaaggt taggtaggcc tggcgatgg ttgtccaggt  1440 gaaagtatgt aggtagaggt gctaggcaaa tccggcatct tgttgatctg agatacgaga  1500
cgaagtcaaa caagtttgac aaagctattg ataccatgct tccaggaaaa gcttctaagt  1560
atattatata agcgaccgta ctgtaaaccg acactggtgg gtaggtagag aatactaagg  1620
ctatgagata actctggtga aggaactagg caaaatgaca ccgtaacttt ggaagaaggt  1680
gtgccattga tggtgatgag acttgctctc tgagctgttg ggggttgcaa ataccaggtg  1740
gctgcgactg tttatcaaaa acacagcact ctgctaaatc gtaagatgaa gtatagggtg  1800
tgacgcctgc ccggtgctgg aaggttaatt gaagggtta gcgcaagcga agctctggat  1860
cgaagcccca gtaaacggcg gccgtaacta taacggtcct aaggtagcga aattccttgt  1920
cgggtaagtt ccgacctgca cgaatggcgt aacgacggcc acactgtctc caccagag    1978
```

-continued

```
<210> SEQ ID NO 4
<211> LENGTH: 19
<212> TYPE: DNA
<213> ORGANISM: Francisella nsp.

<400> SEQUENCE: 4
gattaaaggt ggcctttgt                                                    19

<210> SEQ ID NO 5
<211> LENGTH: 19
<212> TYPE: DNA
<213> ORGANISM: Francisella nsp.

<400> SEQUENCE: 5
ttggattagc tagttggta                                                    19

<210> SEQ ID NO 6
<211> LENGTH: 18
<212> TYPE: DNA
<213> ORGANISM: Francisella nsp.

<400> SEQUENCE: 6
cctcagtgtc agtattga                                                     18

<210> SEQ ID NO 7
<211> LENGTH: 20
<212> TYPE: DNA
<213> ORGANISM: Francisella nsp.

<400> SEQUENCE: 7
cctacaagct attaacttat                                                   20

<210> SEQ ID NO 8
<211> LENGTH: 21
<212> TYPE: DNA
<213> ORGANISM: Francisella nsp.

<400> SEQUENCE: 8
acaggtcttc ggatgctgac g                                                 21

<210> SEQ ID NO 9
<211> LENGTH: 19
<212> TYPE: DNA
<213> ORGANISM: Francisella nsp.

<400> SEQUENCE: 9
tcactccgtg gtaaacgcc                                                    19
```

BACTERIUM AND VACCINE

REFERENCE TO SEQUENCE LISTING

The material saved as "text document" under the file name "SubstituteSequenceListing" created on Jan. 5, 2009 is hereby incorporated by reference.

The present invention relates to a novel rod-shaped pleiomorphic non-motile Gram-negative bacterium causing a new, deadly, disease in fish, to a microbiological culture comprising said bacterium, to a vaccine comprising said bacterium and methods for the preparation of such a vaccine, to antibodies reactive with said bacterium, to diagnostic test kits and to the use of said bacterium.

Over the last decades, world-wide a strong increase is seen in the consumption of fish. This equally regards the consumption of cold water fish such as salmon, turbot, halibut and cod, and tropical species such as Asian sea bass, tilapia, milkfish, yellowtail, amberjack, grouper and cobia. As a consequence, a world-wide increase has been seen in the number and the size of fish farms, in order to meet the increasing needs of the market. In the north Atlantic region the major species in production is Atlantic salmon (*Salmo salar*), Rainbow trout (*Oncorhynchus mykiss*), halibut (*Hippoglossus hippoglossus*) and cod (*Gadus morhua*). The production of Atlantic salmon in Norway was 508.000 tons in 2003 while the newly started cod production amounted to 605 tons only. Given the fact that only in the UK, cod consumption is 170.000 tons yearly, and given the sharp reduction in European catch limits, it is clear that cod farming commercially becomes more and more attractive. There certainly is experience in the field of cod farming. Nevertheless, cod farming is still in its infancy because of its complexity and higher expenses involved. Compared to e.g. salmon, young cod is much more vulnerable to diseases. The major problems in cod production are experienced during the start feeding phase and mortality during this stage of production is high. Viral diseases such as Viral Necrosis, bacterial diseases such as vibriosis, fin rot and furunculosis, fungal diseases and ecto- and endoparasites are a constant menace to (young) cod.

As is known from e.g. animal husbandry, if large numbers of animals are living closely together they become vulnerable to all kinds of diseases, even diseases hardly known or seen, or even unknown, before the days of large-scale commercial farming. This is equally the case in fish farming.

SUMMARY OF THE INVENTION

Recently, the inventor found the causative agent of a recently found disease of hitherto unknown origin, further referred to also as Cod's Syndrome in Atlantic cod (*Gadus morhua*). It has now been determined that the causative agent of this disease is a novel rod-shaped pleiomorphic non-motile Gram-negative bacterium. It is an objective of the present invention to provide the causative agent of this enigmatic disease as well as vaccines aiming at combating and preventing the disease. Moreover, it is an objective of the present invention to provide means to detect and identify the causative agent.

BRIEF DESCRIPTION OF THE FIGURES

FIG. 1: alignment of rDNA genes from the new *Francisella* species from Atlantic cod (F nsp) compared to the rDNA genes from a related bacterium isolated from Tilapia in Taiwan.

Figure 2:
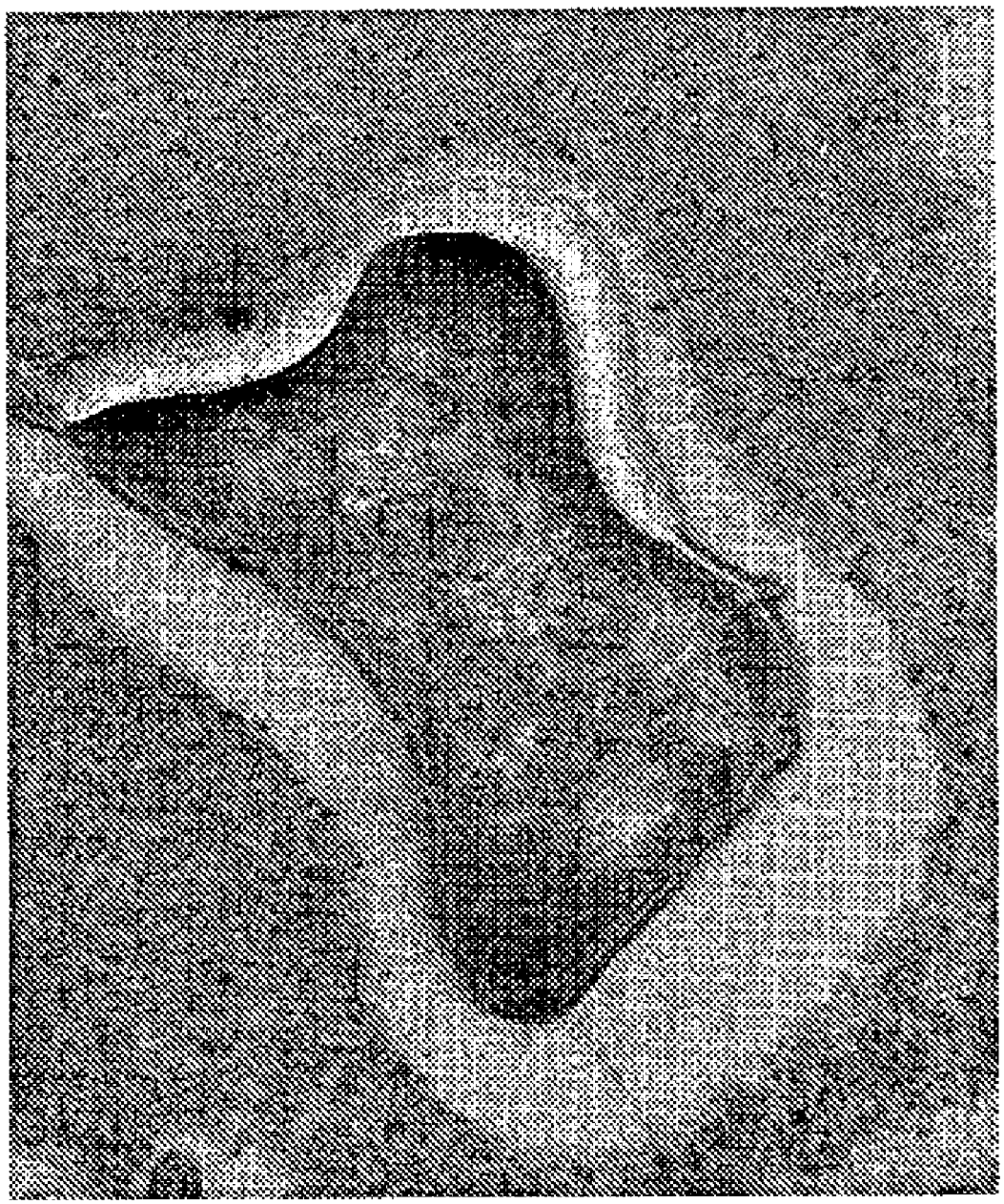
Figure 3:
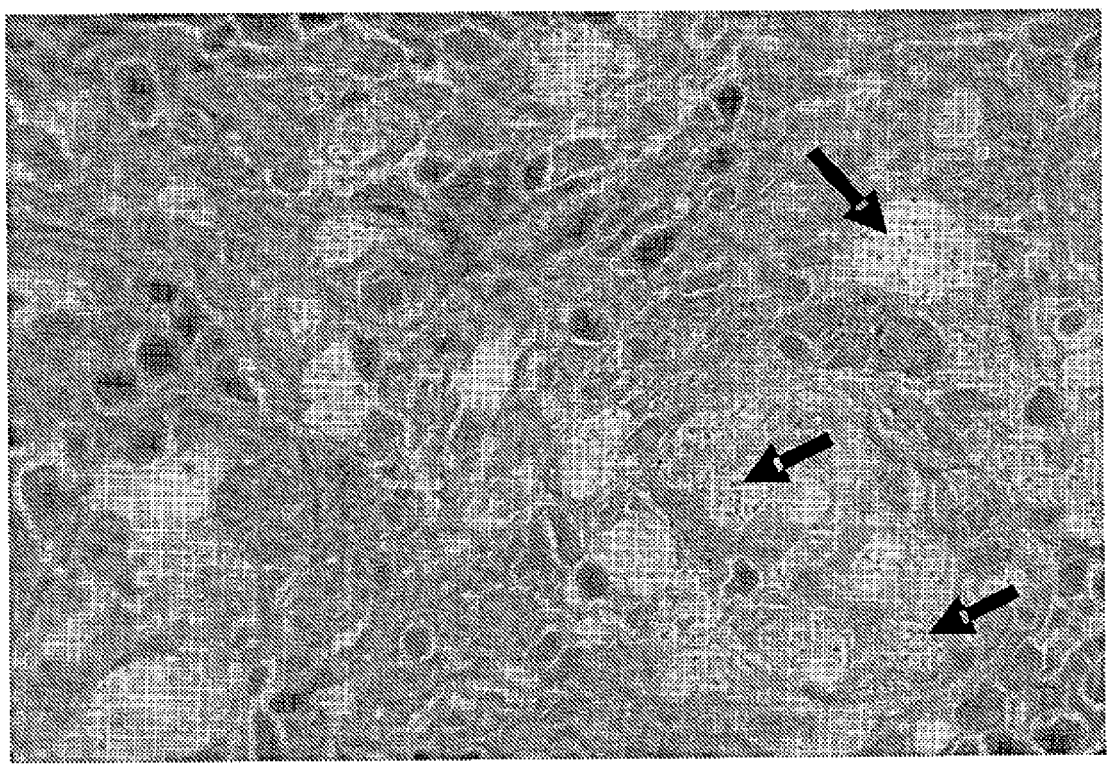
Figure 4:
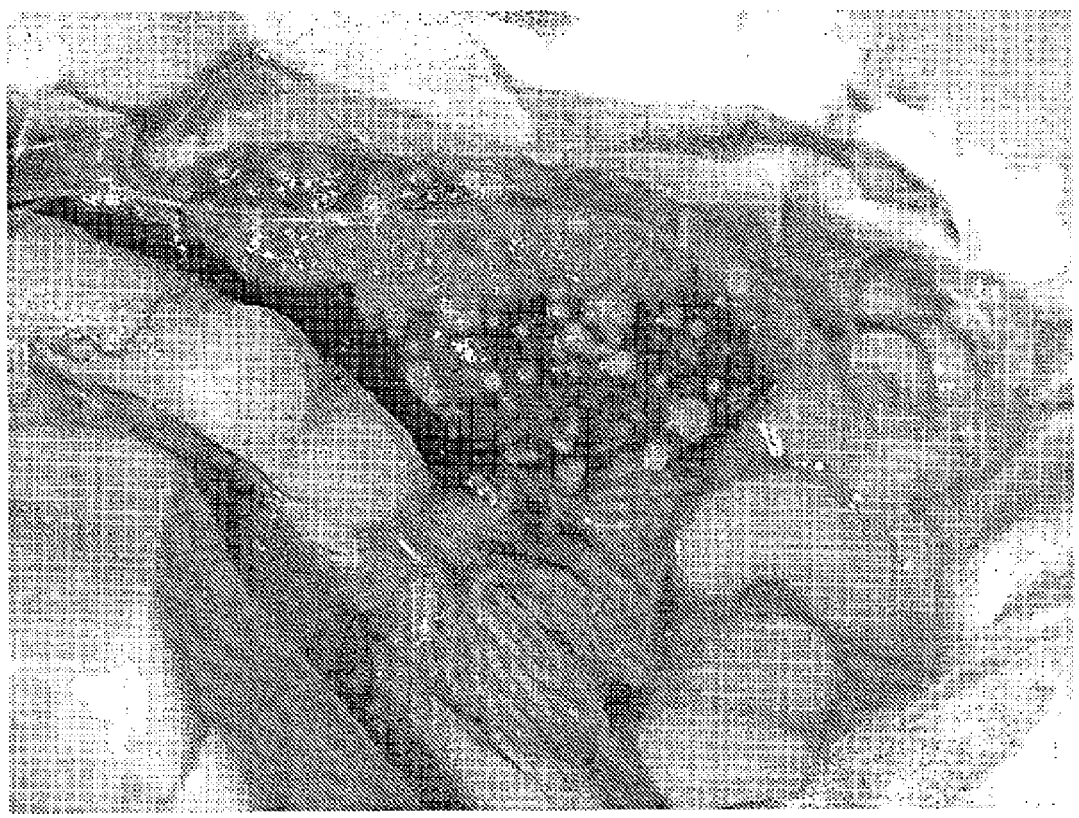
Figure 5:
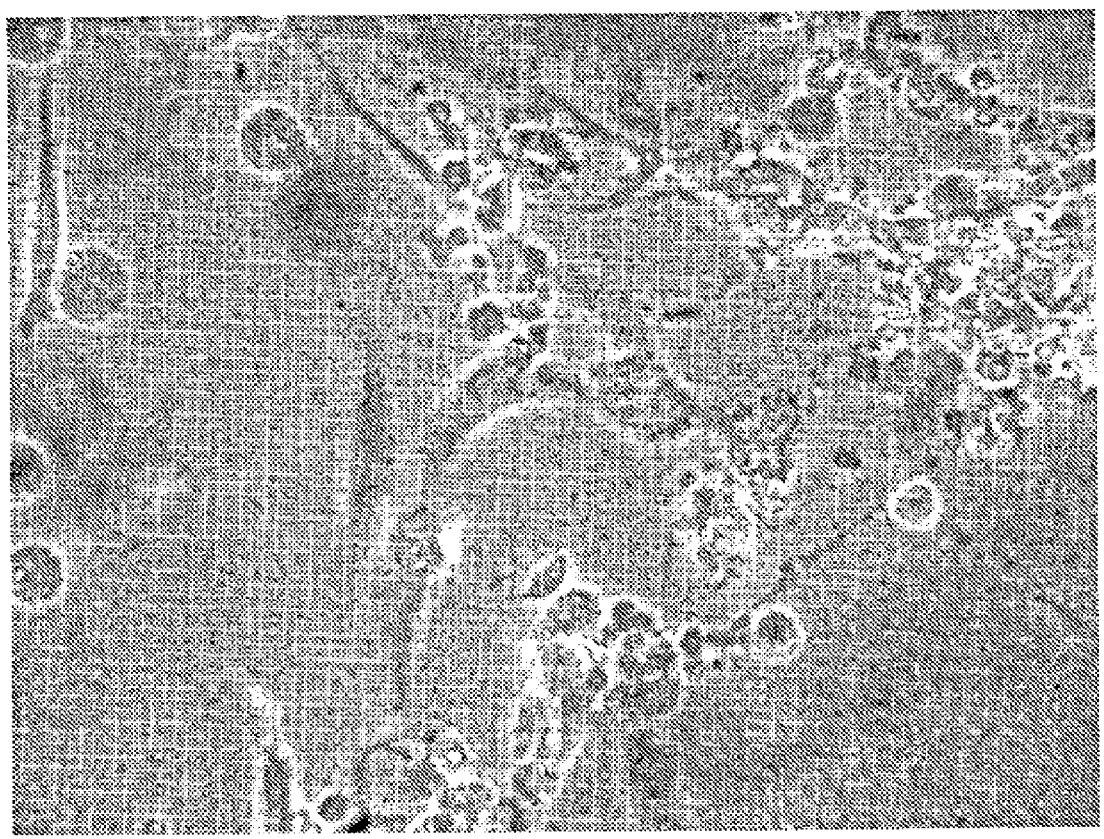

FIG. 2: transmission electron microscopic picture of the bacterium according to the invention.

FIG. 3: histological section through the spleen tissue of chronic infected Atlantic salmon. The arrows indicate the bacteria according to the invention.

FIG. 4: macroscopic picture of the spleen of an infected cod. The specific white nodules can clearly be seen.

FIG. 5: bacteria (indicated by arrows) growing in SHK-1 cells.

FIG. 6: time to onset of mortality and the cumulative mortality over time for Atlantic cod.

FIG. 7: time to onset of mortality and the cumulative mortality over time for Atlantic salmon.

DETAILED DESCRIPTION OF THE EMBODIMENTS

Atlantic cod suffering from this new disease show loss of appetite, reduced swimming performance, and dark pigmentation. There are few other external signs of disease, but white spots may be found on gills and in the mouth cavity. It has been observed that the disease spreads within cod farms. Acute infection can result in mortality within 10 days after challenge, but with few gross clinical signs of disease. The most prominent clinical sign is a swollen and liquefied kidney. Cod suffering from chronic disease may have swollen spleen, kidney and heart. These blood rich organs will in most cases contain white cyst-like inclusions/nodules. The cyst-like structures may contain a transparent liquid. Microscope sections of these tissues show degeneration and proliferation of cells. A few intracellular bacteria may be observed in cells from these tissues. White cyst-like structures may also be found on and in the liver.

The causative agent of this disease is a novel rod-shaped pleiomorphic non-motile Gram-negative bacterium. An example of the DNA sequence of the 16S rRNA gene, the intergenic spacer and the 23S rRNA gene of this novel bacterium is depicted in FIG. 1 and SEQ ID NO 1, SEQ ID NO 2 and SEQ ID NO 3 respectively. SEQ ID NO 1 represents the 16S rRNA gene except for the first 65 nucleotides which are not reproduced here. SEQ ID NO 2 represents the 16S-23S intergenic spacer. SEQ ID NO 3 represents the 23S rRNA gene, except for the last 880 nucleotides which are not reproduced here.

Comparison of these sequences with a genome databank unexpectedly revealed that the bacterium bears a relatively high level of resemblance to a so-called *Rickettsia*-like organism (RLO) found earlier in tropical fish species such as Tilapia.

Therefore, it is now assumed that there might be some evolutionary relationship between the newly identified RLO according to the invention and the RLO described in tropical fish species such as Tilapia. This relationship is surprising, if only because of the differences in growth temperature. Thus, the moment of diversification of the newly identified pathogen and the Tilapia RLO must be early in evolution.

Figure 1A:
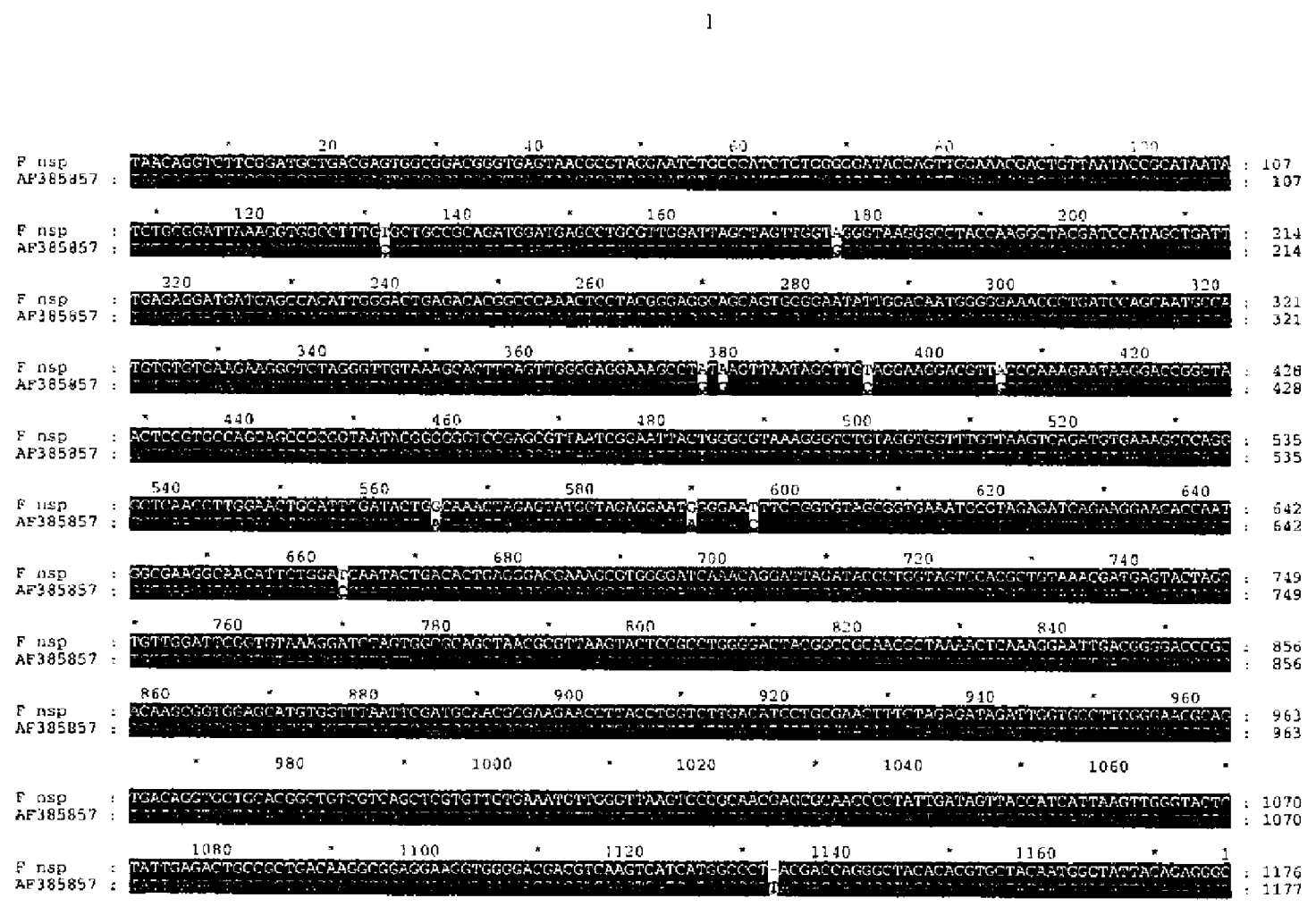
Figure 1B:
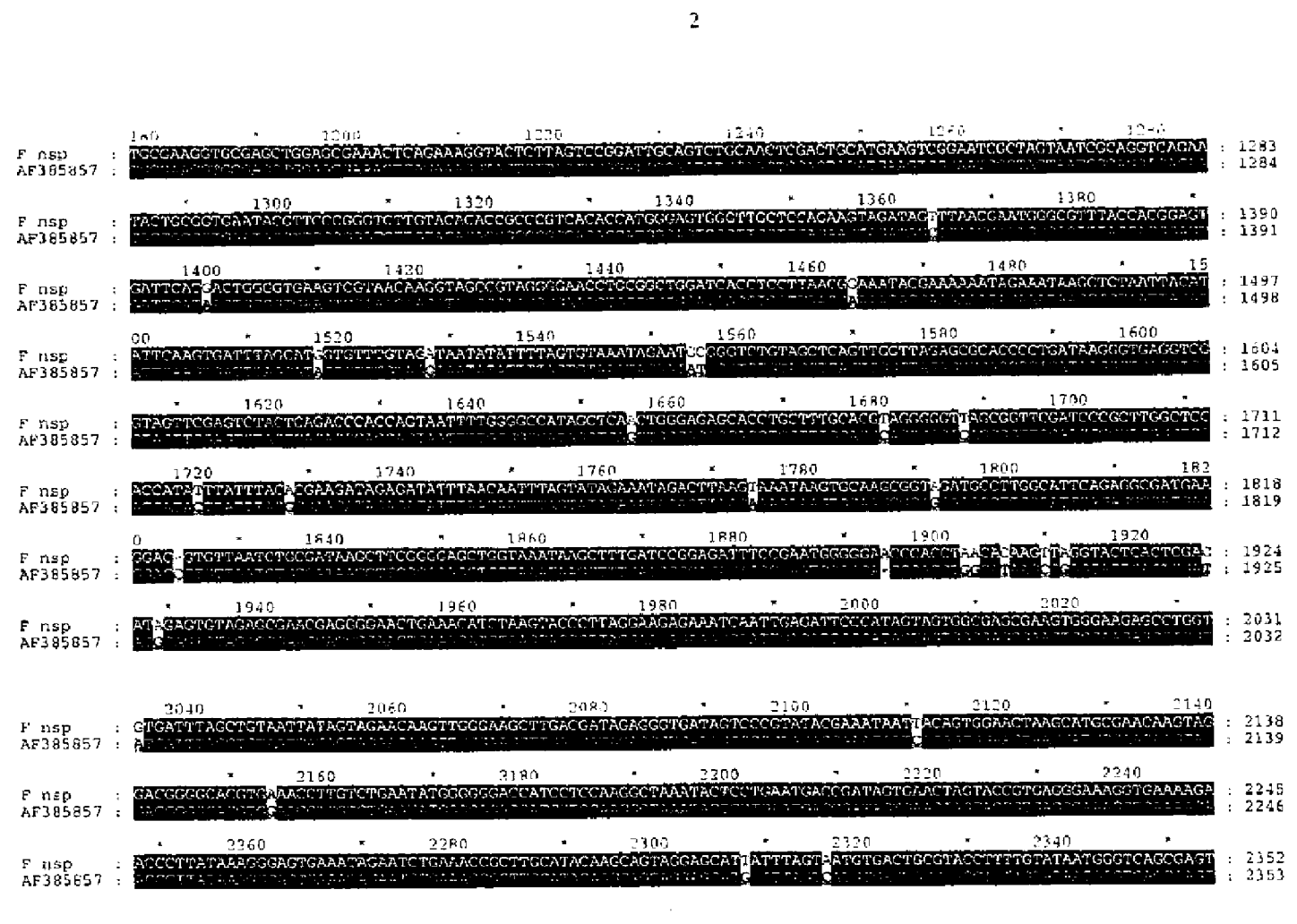
Figure 1C:
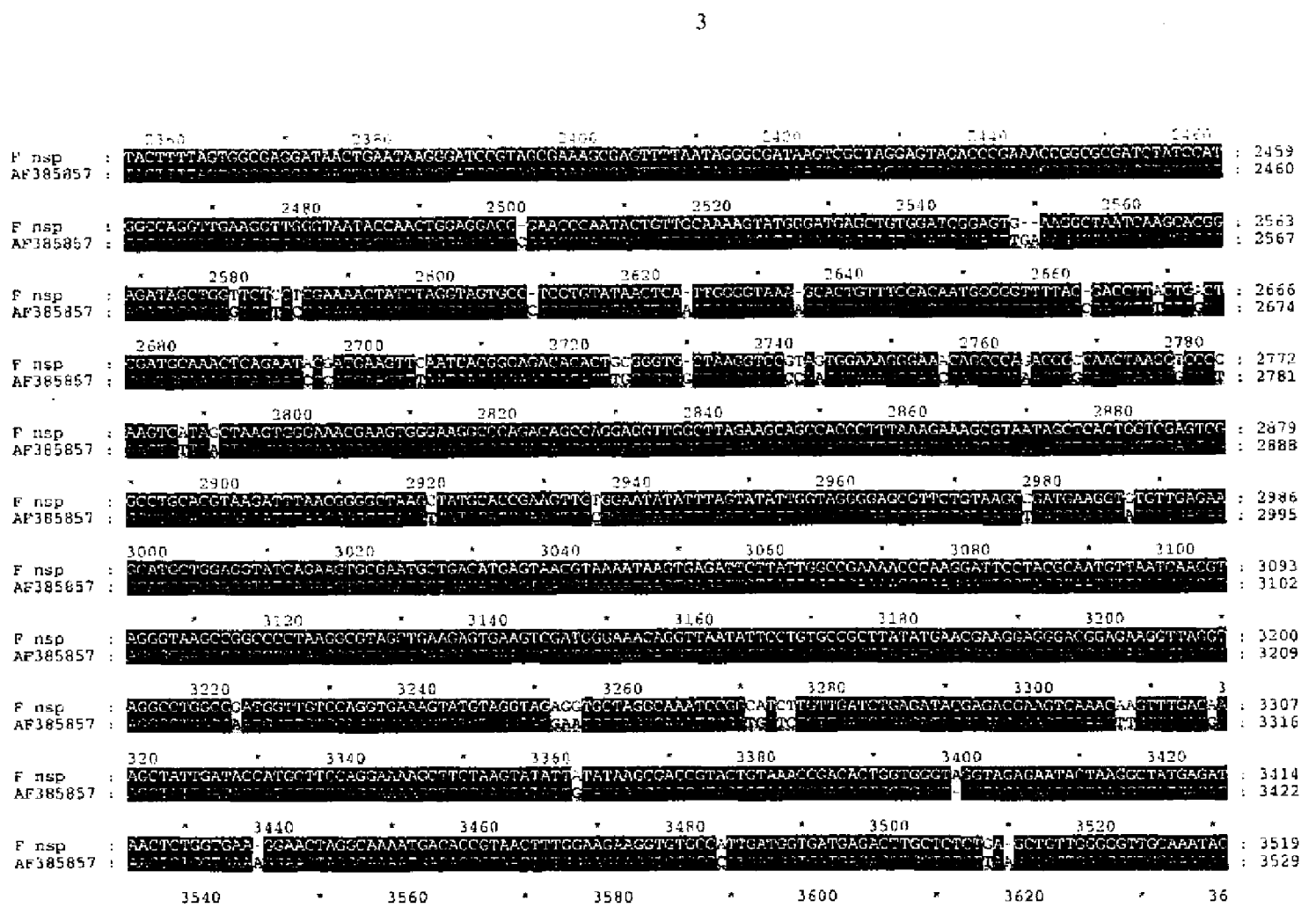
Figure 1D:
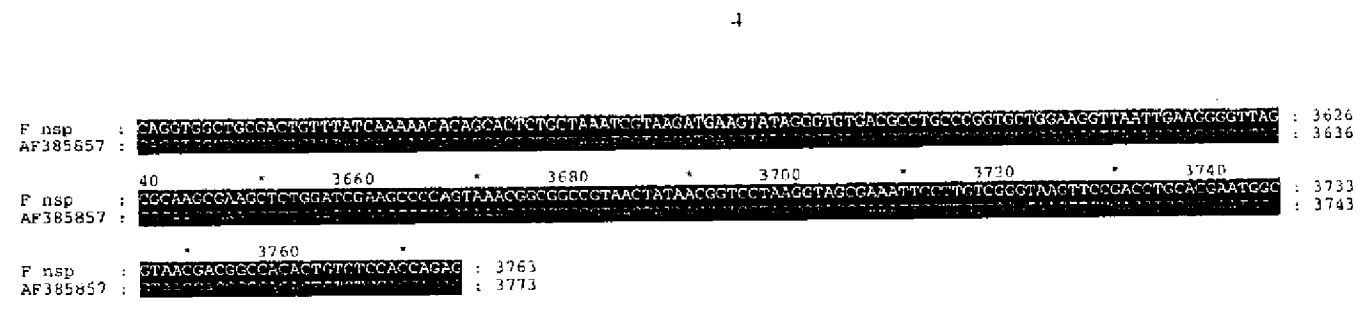

The novel bacterium can be discriminated from the RLO as found in Tilapia on the basis of its 16S rRNA and its 23S rRNA. The 16S rRNA is depicted in SEQ ID NO: 1 and the 23S rRNA is depicted in SEQ ID NO: 3. It turned out that the 16S rRNA of the novel bacterium according to the invention and the Tilapia RLO have a 99% sequence identity, whereas the respective 23S rRNA's have a 96% sequence identity A sequence comparison of the 16S, spacer and 23S rRNA's of the novel bacterium according to the invention and the Tilapia RLO is presented in FIG. 1. This comparison shows the differences in sequence and therefore allows to develop primers that are specific for the novel bacterium found in cod.

The Tilapia RLO has been described i.a. by Chern, R. S. and Chao, C. B. in Fish Pathology 29: 61-71, (1994).

The novel bacterium can i.a. be characterized on the basis of its 16S rRNA or on the basis of its 23S rRNA, and finally it can be characterized by the fact that it specifically reacts with a unique set of primers, as will be explained below.

SEQ ID NO 1 shows a typical example of the nucleotide sequence of by far most of the 16S rRNA gene of a bacterium according to the invention. Natural variations leading to minor changes in the 16S rRNA sequence (or spacer sequence or 23S rRNA sequence) are however found.

It is therefore considered that a rod-shaped pleiomorphic non-motile Gram-negative bacterium causing Cod's Syndrome in fish, of which the nucleotide sequence of the region of the 16S rRNA gene corresponding to the 16S rRNA gene as depicted in SEQ ID NO 1 has a level of identity of at least 99.1%, preferably 99.2%, more preferably 99.3%, 99.4%, 99.5%, 99.6%, 99.7%, 99.8%, 99.9% in increasing order of preference and most preferably 100% with the nucleotide sequence as depicted in SEQ ID NO 1, belongs to the novel bacterium according to the invention.

Thus, a first embodiment of the invention relates to a novel rod-shaped pleiomorphic non-motile Gram-negative bacterium causing Cod's Syndrome in fish, of which the nucleotide sequence of the region of the 16S rRNA gene corresponding to the 16S rRNA gene as depicted in SEQ ID NO 1 has a level of identity of at least 99.1%, preferably 99.2%, more preferably 99.3%, 99.4%, 99.5%, 99.6%, 99.7%, 99.8%, 99.9% in increasing order of preference and most preferably 100% to the nucleotide sequence as depicted in SEQ ID NO 1.

With a level of identity is of course meant the level of identity of the sequence of SEQ ID NO 1 and the corresponding region of the 16S rRNA gene of the bacterium of which the level of identity has to be determined.

Another, alternative way to characterize a novel rod-shaped pleiomorphic non-motile Gram-negative bacterium according to the invention relates to the sequence of the 23S rRNA of the bacterium.

SEQ ID NO 3 shows a typical example of the nucleotide sequence of the 23S rRNA gene of a bacterium according to the invention. Natural variations leading to minor changes in the 23S rRNA sequence are however found.

It is therefore considered that a rod-shaped pleiomorphic non-motile Gram-negative bacterium causing Cod's Syndrome in fish, of which the nucleotide sequence of the region of the 23S rRNA gene corresponding to the 23S rRNA gene as depicted in SEQ ID NO 3 has a level of identity of at least 96.0%, preferably 96.5%, more preferably 97.0%, 97.5%, 98.0%, 98.5%, 99.0%, 99.2%, 99.4%, 99.6%, 99.8%, 99.9% in increasing order of preference and most preferably 100% identical to the nucleotide sequence as depicted in SEQ ID NO 3, belongs to the novel bacterium according to the invention.

Thus, another form of this first embodiment of the invention relates to a novel rod-shaped pleiomorphic non-motile Gram-negative bacterium causing Cod's Syndrome in fish, of which the nucleotide sequence of the region of the 23S rRNA gene corresponding to the 23S rRNA gene as depicted in SEQ ID NO 3 has a level of identity of at least at least 96.0%, preferably 96.5%, more preferably 97.0%, 97.5%, 98.0%, 98.5%, 99.0%, 99.2%, 99.4%, 99.6%, 99.8%, 99.9% in increasing order of preference and most preferably 100% to the nucleotide sequence as depicted in SEQ ID NO 3.

Still another, alternative, way to characterize the novel rod-shaped pleiomorphic non-motile Gram-negative bacterium according to the invention depends on a PCR-test using primer sets that are specific for the 16S rRNA gene sequence of bacteria according to the invention. These primer sets, of which the sequence is depicted in SEQ ID NO 4-7, were selected for their specific selectivity for the novel bacterium. They specifically react with the 16S rRNA gene of the novel bacterium but not with that of closely related Tilapia RLO that does not belong to the bacterium according to the invention. The test, which is described in more detail in the Examples section, is a standard PCR test.

It is therefore considered that a novel rod-shaped pleiomorphic non-motile Gram-negative bacterium causing Cod's Syndrome in fish, of which the 16S rRNA gene reacts in a PCR reaction with primers as depicted in SEQ ID NO.: 4 (CSF-1) or SEQ ID NO.:5 (CSF-2) on the one hand, and SEQ ID NO.: 6 (CSR-1) or SEQ ID NO.: 7 (CSR-2) on the other hand, to give a PCR product of 567+/−10 base pairs (CSF1+CSR1), 523+/−10 base pairs (CSF2+CSR1), 283+/−10 base pairs (CSF1+CSR2) or 239+/−10 base pairs (CSF2+CSR2) is considered to belong to the novel bacterium of the invention.

Thus, again another form of the first embodiment also relates to a novel rod-shaped pleiomorphic non-motile Gram-negative bacterium causing Cod's Syndrome in fish, of which the 16S rRNA gene reacts in a PCR reaction with a primer as depicted in SEQ ID NO 4 or 5, and with a primer as depicted in SEQ ID NO 6 or 7 to give a PCR product of 567+/−10 base pairs (CSF1+CSR1), 523+/−10 base pairs (CSF2+CSR1), 283+/−10 base pairs (CSF1+CSR2) or 239+/−10 base pairs (CSF2+CSR2).

A preferred form of this embodiment relates to a novel rod-shaped pleiomorphic non-motile Gram-negative bacterium causing Cod's Syndrome in fish, of which the nucleotide sequence of the region of the 16S rRNA gene corresponding to the 16S rRNA gene as depicted in SEQ ID NO 1 has a level of identity of at least 99.1%, preferably 99.2%, more preferably 99.3%, 99.4%, 99.5%, 99.6%, 99.7%, 99.8%, 99.9% in increasing order of preference and most preferably 100% to the nucleotide sequence as depicted in SEQ ID NO 1 and of which the nucleotide sequence of the region of the 23S rRNA gene corresponding to the 23S rRNA gene as depicted in SEQ ID NO 3 has a level of identity of at least at least 96.0%, preferably 96.5%, more preferably 97.0%, 97.5%, 98.0%, 98.5%, 99.0%, 99.2%, 99.4%, 99.6%, 99.8%, 99.9% in increasing order of preference and most preferably 100% to the nucleotide sequence as depicted in SEQ ID NO 3.

A more preferred form of this embodiment relates to a novel rod-shaped pleiomorphic non-motile Gram-negative bacterium causing Cod's Syndrome in fish, of which the nucleotide sequence of the region of the 16S rRNA gene corresponding to the 16S rRNA gene as depicted in SEQ ID NO 1 has a level of identity of at least 99.1%, preferably 99.2%, more preferably 99.3%, 99.4%, 99.5%, 99.6%, 99.7%, 99.8%, 99.9% in increasing order of preference and most preferably 100% to the nucleotide sequence as depicted in SEQ ID NO 1 and of which the nucleotide sequence of the region of the 23S rRNA gene corresponding to the 23S rRNA gene as depicted in SEQ ID NO 3 has a level of identity of at least at least 96.0%, preferably 96.5%, more preferably 97.0%, 97.5%, 98.0%, 98.5%, 99.0%, 99.2%, 99.4%, 99.6%, 99.8%, 99.9% in increasing order of preference and most preferably 100% to the nucleotide sequence as depicted in SEQ ID NO 3 and of which the 16S rRNA gene reacts in a PCR reaction with a primer as depicted in SEQ ID NO 4 or 5, and with a primer as depicted in SEQ ID NO 6 or 7 to give a PCR product of 567+/−10 base pairs (CSF1+CSR1), 523+/−10 base pairs (CSF2+CSR1), 283+/−10 base pairs (CSF1+CSR2) or 239+/−10 base pairs (CSF2+CSR2).

In an even more preferred form of this embodiment, the bacterium according to the invention is in an inactivated form, for reasons which will be explained below.

In another more preferred form of this embodiment, the bacterium according to the invention is in a live attenuated form, for reasons which will be explained below.

It is one of the merits of the present invention that the hitherto unknown causative agent of the disease has now been unambiguously determined, confirmed by Koch's postulates. Now that the cause of the disease has been found and could be demonstrated to be of bacterial origin, the disease could deliberately be induced and the typical signs of the disease described were seen as expected.

Up till now, the disease is seen in cod. Surprisingly however, it was found that the disease can also be induced in salmon.

After intraperitoneal infection of Atlantic salmon these fish die without any clear clinical signs of disease. Microscopy of the blood rich organs spleen, kidney and heart reveals much less bacteria than observed for cod in the acute phase of infection.

In co-habitants the development of the disease was different from that observed in fish challenged by an intraperitoneal injection. Some of the co-habitants survived for up to 4 months developing more and more signs of disease before dying with distinct pathological changes in the pseudobranchs, gills, kidneys and spleen.

These results demonstrate the ability of this pathogen to seriously affect the two most economical valuable species in the Norwegian fish farming industry.

It is probably only a matter of time before the disease will be demonstrated in other cultured aquatic species.

The newly discovered causative agent of the syndrome is now determined to be a novel rod-shaped pleiomorphic non-motile Gram-negative bacterium, as mentioned above. The novel bacterium is found both freely in/between the tissues and intracellular inside host cell, apparently in vacuoles. The novel bacterium is highly pleiomorphic. The coccoid stages are around 0.5-0.8 µm (these are found when culturing the bacteria on blood agar), while the elongate stages (commonly found in fish and in cell cultures) are generally spoken 1-2 µm long and 0.5-0.9 µm wide.

An example of the novel bacteria has been deposited with the Collection Nationale de Cultures de Microorganisms (CNCM), Institut Pasteur, 25 Rue du Docteur Roux, F-75724 Paris Cedex 15, France, under accession number CNCM I-3511.

As can be seen in the dendrogram below, the novel bacterium according to the invention, the cause of Cod's Syndrome, as exemplified by the deposited strain forms a distinguished species, which is closely related to *Francisella philomiragia* and the Tilapia RLO described above.

The meaning of those numbers that are not explained in the dendrogram is as follows: AY 375394, AY 375395, AY 375396; *Francisella* endosymbiont of *Dermacentor albipictus*, AF001077; *Francisella* endosymbiont of *Dermacentor andersoni*, AY375402; *Francisella* endosymbiont of *Dermacentor occidentalis*, AY375405; *Francisella* endosymbiont of *Dermacentor variabilis*, AB001522: *Ornithodoros moubata* symbiote, AY375407: *Francisella* endosymbiont of *Amblyomma maculatum*, WLBRRBSA; *Wolbachia persica*.

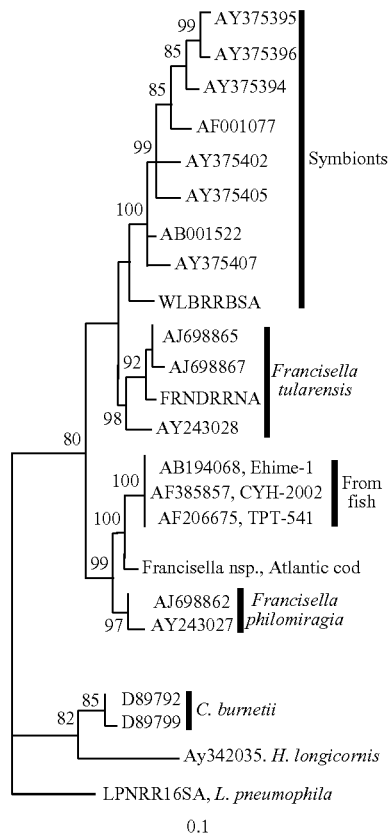

Basically, a typical PCR-based test suitable for the discrimination between the novel bacterium according to the invention and other pathogens could be based upon the following:

The primer sets to be used in the test are CSF1 or CSF2 as forward primer and CSR1 or CSR2 as backward primer (see below):

| | | |
|---|---|---|
| CSF-1 | 5' GATTAAAGGTGGCCTTTGT (SEQ ID NO 4) | Forward |
| CSF-2 | 5' TTGGATTAGCTAGTTGGTA (SEQ ID NO 5) | Forward |
| CSR-1 | 5' CCTCAGTGTCAGTATTGA (SEQ ID NO 6) | Reversed |
| CSR-2 | 5' CCTACAAGCTATTAACTTAT (SEQ ID NO 7) | Reversed |

A small portion of a colony, but at least 10 cells, preferably $10^3$ cell (volume about 1 µl), is to be picked from a suitable agar plate (see Examples) and transferred to a tube containing puReTaq Ready-To-Go PCR beads dissolved in 23 µl of double distilled water (Amersham Biosciences Cat no. 27-9558-01). Subsequently, 0.5 µl of each of the primers BBF-1 with BBR-4 (10 µl stock solution) is added. The sample is subsequently run using a thermal cycler with the following settings:

| | | | |
|---|---|---|---|
| Denaturation | 95° C. | 2 mins | ×1 cycle |
| Amplification | 95° C. | 30 secs | |
| | 52° C. | 45 secs | ×30 cycles |
| | 72° C. | 45 secs | |
| Extension | 72° C. | 5 mins | ×1 cycle |

PCR-techniques are extensively described in text books such as Dieffenbach & Dreksler; PCR primers, a laboratory manual. ISBN 0-87969-447-5 (1995).

If analysis of the PCR-product reveals a PCR product of approximately 567 base pairs (using primers F1 and R1), approximately 523 base pairs (using primers F2 and R1), approximately 283 base pairs (using primers F1 and R2) or approximately 239 base pairs (using primers F2 and R2), this unequivocally demonstrates that the analysed bacterium belongs to the novel bacterium according to the invention. A PCR product of approximately 567 base pairs is a PCR product with a length of 567+/−10 base pairs, and thus with a length of between 557 and 587 base pairs.

In principle, the length of the PCR fragments is more likely to be the expected length+/−2 nucleotides, or even exactly the expected length. The +/−10 margin is mainly mentioned here because some variation in the region between the spacer regions may exist in variants of the novel bacterium according to the invention.

As is known to the skilled artisan, due to slight changes in salt concentration or temperature of the PCR reaction, non-specific PCR-fragments of the same length as indicated above may occur, if the test described above is performed with other bacteria not belonging to the novel species according to the invention. Therefore, the following should be take into account when using a PCR test to determine if a bacterium belongs to the novel bacterium according to the invention or not: the PCR test must include a positive control PCR reaction mix and a negative control PCR reaction mix. These reaction mixes differ only in one respect from the reaction mix of the bacterium to be tested: the negative control mix comprises a Tilapia RLO 16S rRNA gene and the positive control mix comprises a 16S rRNA gene of a bacterium according to the invention. If the positive reaction mix gives a PCR-product of the expected size, and the negative reaction mix gives no PCR product, it can be assumed that the PCR-conditions for the reaction mix of the bacterium to be tested are right.

As will be discussed in extenso in the Examples below, another of the merits of the present invention is, that a suitable growth medium for the bacterium according to the invention has now been found. Bacteria according to the invention can now be grown in vitro.

The skilled person finds in the Examples below a method for the isolation of the bacterium according to the invention from diseased fish, as well as for further growth of the bacterium on suitable medium.

Therefore, another embodiment of the present invention relates to a microbial culture comprising a bacterium according to the invention.

It is again one of the merits of the present invention that, the causative agent being known now, the development of vaccines became feasible. The strong immune response triggered in infected survivor fish (fish that survive a first infection), which leads to the induction of immunity against a second infection with the bacterium according to the invention is in itself already an indication that vaccination is feasible. The problem encountered in the natural course of the disease however is, that the onset of an adequate immune response usually is too slow. An adequate immune response, i.e. a response that suppresses the infection to at least a level that enables the fish to survive the infection, takes time to build up. Under natural conditions, this time is usually not available due to the very rapid progress of the disease: 90% of the infected fish die within days. Because the pathogen causing the disease has now been identified, a vaccine based upon this pathogen solves this problem because after vaccination, the immunological defense against the bacterium can build up before a natural infection strikes.

Thus, another embodiment of the present invention relates to a vaccine for combating the disease; Cod's Syndrome, as caused by the novel bacterium, wherein said vaccine comprises a bacterium according to the invention and a pharmaceutically acceptable carrier.

The vaccine according to the invention may comprise the bacteria in attenuated live or inactivated form. Attenuated live vaccines, i.e. vaccines comprising the bacterium according to the invention in a live attenuated form, have the advantage over inactivated vaccines that they best mimic the natural way of infection. In addition, their replicating abilities allow vaccination with low amounts of bacteria; their number will automatically increase until it reaches the trigger level of the immune system. From that moment on, the immune system will be triggered and will finally eliminate the bacteria. A minor disadvantage of the use of live attenuated bacteria however might be that inherently there is a certain level of virulence left. This need not be a real disadvantage as long as the level of virulence is acceptable, i.e. as long as the vaccine at least prevents the fish from dying. Of course, the lower the rest virulence of the live attenuated vaccine is, the less influence the vaccination has on weight gain during/after vaccination.

Therefore, one preferred form of this embodiment of the invention relates to a vaccine comprising a bacterium according to the invention in a live attenuated form.

A live attenuated bacterium is a bacterium that has a decreased level of virulence when compared to field strains. As mentioned above, the virulence of field strains of the novel bacterium according to the invention is very high: mortality typically exceeds 70% of all infected fish. A bacterium having a decreased level of virulence is considered a bacterium that only induces disease to the extent that mortality does not exceed 10%, and 90% of all infected fish survive the infection. Bacteria often behave attenuated as a result of a decreased growth rate. If such bacteria are used as the basis of an attenuated live vaccine, contrary to the situation described earlier, the immune system is triggered to the level necessary to suppress the disease before the fish die. As a result, the fish will not only survive but additionally, they build up immunity against future infections with a fully virulent field strain. Attenuated strains can e.g. be obtained by growing the bacteria according to the invention in the presence of a mutagenic agent. Many of such agents are known in the art and methods for the attenuation of bacteria using such agents have been known in the art for decades. Another way of obtaining mutated bacteria is to subject them to growth under temperatures exceeding the temperature of their natural habitat. Yet another way of mutating bacteria well-known in the art is transposon-mutagenesis.

Selection methods for slow-growing mutants or for temperature sensitive mutants (Ts-mutants) are also well-known in the art. Merely as an example: a suitable method for selection of slow-growing mutants simply relies on the plating of bacteria treated with a mutagen followed, after incubation, by visual selection of small colonies. Such colonies are slow-growing and thus they form the desired live attenuated bacteria. Selection for Ts-mutants is equally easy: replica-plating of bacteria treated with a mutagen followed by incubation at a sub-optimal (2-4 degrees below native growth temperature) or the optimal temperature, followed by visual selection of those colonies that did grow normal speed under sub-optimal temperature but did grow slower at the optimal temperature.

Inactivated vaccines are, in contrast to their live attenuated counterparts, inherently safe, because there is no rest virulence left. In spite of the fact that they usually comprise a somewhat higher dose of bacteria compared to live attenuated vaccines, they may e.g. be the preferred form of vaccine in fish that are suffering already from other diseases. Fish that are kept under sub-optimal conditions, such as incomplete nutrition or sub-optimal temperatures, would also benefit from inactivated vaccines.

Therefore, another preferred form of this embodiment relates to a vaccine comprising a bacterium according to the invention in an inactivated form.

Many physical and chemical methods of inactivation of bacteria are nowadays known in the art. Examples of physical inactivation are UW-radiation, X-ray radiation, gamma-radiation and heating. Examples of inactivating chemicals are β-propiolactone, glutaraldehyde, binary ethylene-imine and formaldehyde. The skilled person would undoubtedly know how to apply these methods. Preferably the strain is inactivated with β-propiolactone, glutaraldehyde, ethylene-imine or formaldehyde. Of these, β-propiolactone and ethylene-imine are the most preferred. It is obvious that other ways of inactivating the bacteria are also embodied in the present invention. Vaccines comprise the bacterium according to the invention in an attenuated live and/or killed form, and in addition they comprise a pharmaceutically acceptable carrier. A pharmaceutically acceptable carrier can be as simple as e.g. distilled water or a physiological salt solution. It can also be e.g. a buffer solution.

Vaccines according to the present invention may in a preferred presentation also contain an immunostimulatory substance, a so-called adjuvant. Adjuvants in general comprise substances that boost the immune response of the host in a non-specific manner. A number of different adjuvants are known in the art. Examples of adjuvants frequently used in fish and shellfish farming are muramyldipeptides, lipopolysaccharides, several glucans and glycans and Carbopol® (a homopolymer). An extensive overview of adjuvants suitable for fish and shellfish vaccines is given in the review paper by Jan Raa (Reviews in Fisheries Science 4(3): 229-288 (1996)). The vaccine may also comprise a so-called "vehicle". A vehicle is a compound to which the bacterium adheres, without being covalently bound to it. Such vehicles are i.a. bio-microcapsules, micro-alginates, liposomes and macrosols, all known in the art. A special form of such a vehicle, in which the antigen is partially embedded in the vehicle, is the so-called ISCOM (EP 109.942, EP 180.564, EP 242.380) In addition, the vaccine may comprise one or more suitable surface-active compounds or emulsifiers, e.g. Span or Tween.

Oil adjuvants suitable for use in water-in-oil emulsions are e.g. mineral oils or metabolisable oils. Mineral oils are e.g. Bayol®, Marcol® and Drakeol®. Metabolisable oils are e.g. vegetable oils, such as peanut oil and soybean oil, animal oils such as the fish oils squalane and squalene, and tocopherol and its derivatives. Suitable adjuvants are e.g. w/o emulsions, o/w emulsions and w/o/w double-emulsions Very suitable o/w emulsions are e.g. obtained starting from 5-50% w/w water phase and 95-50% w/w oil adjuvant, more preferably 20-50% w/w water phase and 80-50% w/w oil adjuvant.

The amount of adjuvant added depends on the nature of the adjuvant itself, and information with respect to such amounts will be provided by the manufacturer.

Often, the vaccine is mixed with stabilisers, e.g. to protect the bacteria from being degraded, to enhance the shelf-life of the vaccine, or to improve freeze-drying efficiency. Useful stabilisers are i.a. SPGA, carbohydrates e.g. sorbitol, mannitol, trehalose, starch, sucrose, dextran or glucose, proteins such as albumin or casein or degradation products thereof, and buffers, such as alkali metal phosphates.

Preferably, vaccines according to the invention are stored/presented in a freeze-dried form.

In addition, the vaccines may be suspended in a physiologically acceptable diluent. It goes without saying, that other ways of adjuvating, adding vehicle compounds or diluents, emulsifying or stabilizing are also embodied in the present invention.

Vaccines based upon inactivated bacteria can in principle be administered in doses between $10^3$ and $10^9$ CFU bacteria. Doses below $10^3$ bacteria might, depending i.a. on the method of inactivation, not be sufficiently immunogenic, and doses that exceed $10^9$ bacteria would from a commercial point of view not be very attractive. Although suitable amounts would range between $10^3$ and $10^9$ CFU bacteria, amounts between $10^5$ and $10^8$ CFU are preferred amounts.

Vaccines based upon live attenuated bacteria can in principle be administered in lower doses, because the bacteria multiply themselves during the infection. Therefore, although suitable amounts would range between $10^3$ and $10^9$ CFU bacteria, amounts between $10^3$ and $10^6$ CFU are preferred amounts.

Many ways of administration, all known in the art can be applied. The vaccines according to the invention are preferably administered to the fish via injection, immersion, dipping or per oral. Injection is more labor-intensive, and is primarily applied for the administration of inactivated vaccines. Administration by immersion, dipping or per oral is the most preferred way of administration for live attenuated vaccines because it is quick and allows mass application, and is very suitable for very young/small fish, for which injection is not practical.

The administration protocol can be optimized in accordance with standard vaccination practice. Preferably the vaccine is administered via immersion or per oral, especially in case of the use of vaccines in commercial aquaculture farms. For oral administration the vaccine is preferably mixed with a suitable carrier for oral application i.e. cellulose, food or a metabolisable substance such as alpha-cellulose or different oils of vegetable or animals origin. Also an attractive way is administration of the vaccine to high concentrations of live-feed organisms, followed by feeding the live-feed organisms to the target animal, e.g. the fish. Particularly preferred food carriers for oral delivery of the vaccine according to the invention are live-feed organisms which are able to encapsulate the vaccine. Suitable live-feed organisms include plankton-like non-selective filter feeders preferably members of *Rotifera, Artemia*, and the like. Highly preferred is the brine shrimp *Artemia* sp.

The administration protocol can be optimized in accordance with standard vaccination practice. A recent overview of fish vaccination, written by Bowden et al., (Fisheries Research Service Marine Laboratory, Aberdeen, Scotland) is available from www.intrafish.com.

The age of the fish to be vaccinated is not critical, although clearly one would want to vaccinate against Cod's Syndrome in an early stage. In principle, it would be tempting to vaccinate fish preferably at 0.2 grams, but certainly before 5 grams of weight. Fish having a weight of <0.5 grams however are assumed to be insufficiently immune competent. Therefore, in practice, one would vaccinate fish from 0.5 upwards. Since it is one of the merits of the present invention that it is now possible to perform early diagnosis of the bacterium and of the disease, control measurements such as sanitation can be developed in order to postpone outbreaks until fish have been vaccinated.

It would be beneficial to add to a vaccine, together with bacteria according to the invention, also at least one other fish-pathogenic microorganism or virus, an antigen of such microorganism or virus or genetic material encoding such an antigen in a combination-vaccine.

Examples of notorious commercially important fish pathogens are *Vibrio anguillarum, Aeromonas salmonicidae, Vibrio salmonicidae, Moritella viscose, Vibrio ordalii, Flavobacterium* sp., *Flexibacter* sp., *Streptococcus* sp., *Lactococcus garviae, Edwardsiella tarda, E. ictaluri, Piscirickettsia salmonis*, SPD virus, SD virus, VNN virus, IPN virus and iridoviruses.

The advantage of such a combination vaccine is that it not only provides protection against Cod's Syndrome, but also against other diseases.

Therefore, a preferred form of this embodiment relates to a vaccine wherein that vaccine comprises at least one other microorganism or virus that is pathogenic to fish, or one other antigen or genetic material encoding said other antigen, wherein said other antigen or genetic material is derived from a virus or microorganism pathogenic to fish.

Thus, in a more preferred form of this embodiment, the other microorganism or virus is selected from the following group of notorious commercially important fish pathogens: *Vibrio anguillarum, Aeromonas salmonicidae, Vibrio salmonicidae, Moritella viscose, Vibrio ordalii, Flavobacterium* sp., *Flexibacter* sp., *Streptococcus* sp., *Lactococcus garviae, Edwardsiella tarda, E. ictaluri, Piscirickettsia salmonis*, SPD virus, SD virus, VNN virus, IPN virus and iridoviruses.

All vaccines described above contribute to active vaccination, i.e. they trigger the host's defense system.

Alternatively, antibodies can be raised against the bacterium according to the invention in e.g. rabbits or can be obtained from antibody-producing cell lines as described below. Such antibodies can then be administered to the fish. This method of vaccination, passive vaccination, is the vaccination of choice when an animal is already infected, and there is no time to allow the natural immune response to be triggered. It is also the preferred method for vaccinating animals that are prone to sudden high infection pressure. The administered antibodies reactive with the bacterium according to the invention can in these cases interfere with the bacterium according to the invention and thus suppress Cod's Syndrome. This approach has the advantage that it decreases or stops Cod's Syndrome development, independent of the fish' immune status.

Therefore, one other form of this embodiment of the invention relates to a vaccine for combating Cod's Syndrome that comprises antibodies reactive with bacteria according to the invention and a pharmaceutically acceptable carrier.

Still another embodiment of this invention relates to antibodies reactive with bacteria according to the invention.

Antibodies or antiserum against bacteria according to the invention can be obtained quickly and easily by vaccination of e.g. pigs, poultry or e.g. rabbits with inactivated bacteria according to the invention in e.g. a water-in-oil suspension followed, after about four weeks, by bleeding, centrifugation of the coagulated blood and decanting of the sera. Such methods of raising antibodies are well-known in the art for decades.

Another source of antibodies is the blood or serum of e.g. cod or salmon that have been naturally infected with bacteria according to the invention. Other methods for the preparation of antibodies, which may be polyclonal, monospecific or monoclonal (or derivatives thereof) are well-known in the art. If polyclonal antibodies are desired, techniques for producing and processing polyclonal sera are well-known in the art (e.g. Mayer and Walter, eds. Immunochemical Methods in Cell and Molecular Biology, Academic Press, London, 1987). Monoclonal antibodies, reactive against the novel bacterium according to the invention can be prepared by immunizing inbred mice by techniques also known in the art (Kohler and Milstein, Nature, 256, 495-497, 1975).

A vaccine can also be prepared using antibodies prepared from eggs of chickens that have been vaccinated with a vaccine according to the invention (IgY antibodies).

Preferably a vaccine for oral administration of the antibodies is prepared, in which the antibodies are mixed with an edible carrier such as fish food.

Still another embodiment relates to a method for the preparation of a vaccine according to the invention that comprises the admixing of a bacterium according to the invention and a pharmaceutically acceptable carrier.

Still another embodiment relates to a method for the preparation of a vaccine according to the invention that comprises the admixing of antibodies reactive with a bacterium according to the invention and a pharmaceutically acceptable carrier.

Again another embodiment of the present invention relates to bacteria according to the invention for use in a vaccine.

Still another embodiment of the present invention relates to the use of a bacterium according to the invention for the manufacture of a vaccine for combating Cod's Syndrome.

As mentioned above, lethality after bacterial infection can easily be up to 70-90% and can even reach 100%. In addition to this, disease strikes at a dramatically high speed. Thus, for efficient protection against disease, a quick and correct diagnosis of Cod's Syndrome is important.

Therefore it is another objective of this invention to provide diagnostic tools suitable for the detection of Cod's Syndrome.

A diagnostic test kit based upon the detection of a bacterium according to the invention or antigenic material of that bacterium and therefore suitable for the detection of bacterial infection may i.a. comprise a standard ELISA test. In one example of such a test the walls of the wells of an ELISA plate are coated with antibodies directed against the bacterium. After incubation with the material to be tested, labeled antibodies reactive with the bacterium are added to the wells. A color reaction then reveals the presence of antigenic material of the bacterium. Therefore, still another embodiment of the present invention relates to diagnostic test kits for the detection of a bacterium according to the invention or antigenic material of that bacterium. Such test kits comprise antibodies reactive with a bacterium according to the invention or antigenic material thereof. Antigenic material of the bacterium is to be interpreted in a broad sense. It can be e.g. the bacterium in a disintegrated form, or bacterial envelope material comprising bacterial outer membrane proteins, just to name a few. As long as the material of the bacterium reacts with antiserum raised against the bacterium, the material is considered to be antigenic material.

A diagnostic test kit based upon the detection in serum of antibodies reactive with the bacterium according to the invention and therefore suitable for the detection of Cod's Syndrome may also i.a. comprise a standard ELISA test. In such a test the walls of the wells of an ELISA plate can e.g. be coated with the bacterium according to the invention or antigenic material thereof. After incubation with the material to be tested, labeled antibodies reactive with the bacterium according to the invention are added to the wells. A lack of color reaction then reveals the presence of antibodies reactive with he bacterium according to the invention.

Therefore, still another embodiment of the present invention relates to diagnostic test kits for the detection of antibodies reactive with the bacterium. Such test kits comprise the bacterium according to the invention, or antigenic material thereof.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent-, chemoluminescent-, radio-active- or dye molecules.

Suitable methods for the detection of antibodies reactive with a bacterium according to the present invention in the sample include the enzyme-linked immunosorbent assay (ELISA), immunofluorescense test (IFT) and Western blot analysis.

A very quick and easy diagnostic test for diagnosing the presence or absence of a bacterium according to the invention is a PCR test as described above, comprising PCR-primer CSF1 or CSF2 and primer CSR1 or CSR2 as depicted in SEQ ID NO 4-7.

It goes without saying, that more primers can be used than the four primers identified above. The present invention provides for the first time the unique sequence of the 16S rRNA, the Spacer rRNA and the 23S rRNA gene of Cod's Syndrome strains. This allows the skilled person to select without any additional efforts, other selective primers in addition to the four primers shown there. By simple computer-analysis of the rRNA gene sequences provided by the present invention with the, known, rRNA gene sequences of other bacteria, the skilled person is able to develop other specific PCR-primers for diagnostic tests for the detection of a Cod's Syndrome strain and/or the discrimination between Cod's Syndrome strain and other bacterial (fish) pathogens.

PCR-primers that specifically react with the 16S rRNA, the Spacer rRNA or the 23S rRNA gene of Cod's Syndrome strains are understood to be those primers that react only with the 16S rRNA, the Spacer rRNA or the 23S rRNA gene of Cod's Syndrome strains and not with the 16S rRNA, the Spacer rRNA or the 23S rRNA gene of another (fish) pathogenic bacterium, or group of (fish) pathogenic bacteria.

Thus, another embodiment relates to a diagnostic test kit for the detection of a bacterium according to the invention, which test has as a characteristic feature that it comprises PCR-primers that specifically react with the 16S rRNA, the spacer rRNA or the 23S rRNA gene of Cod's Syndrome strains.

A preferred form of this embodiment relates to test kits comprising the specific PCR-primers CSF1, SCF2, CSF3 and CSF4 as depicted in SEQ ID NO 4-7.

EXAMPLES

Example 1

Primary Isolation of the Organisms and Establishment of a Primary Isolation Medium The novel bacterium according to the invention was isolated from the spleen of cod showing the clinical signs of the syndrome. This was done by bringing a sterile needle into the spleen, followed by taking some material from the spleen. This material was directly plated on an agar of 15° C.

It was found that the novel bacterium can be grown at temperatures between 10 and 15° C. on standard blood agar to which 0.1% cystein and 1% glucose are added. (This agar will also be referred to as Blood agar+cys+glu).

The novel bacterium according to the invention turned out to grow not only on a bacterial growth medium. Surprisingly it was found that intracellular growth of the bacterium is also possible. Suitable cells for growth of the bacterium are e.g. SHK-1 cells (head kidney cells from Atlantic salmon, *Salmo salar*), growing at the same temperature range. Growing SHK-1 cells has been described i.a. by Dannevig B. H., et al., in J. Gen. Virol 76: 1353-1359 (1995) and by Dannevig B. H., et al., in Fish and Shellfish Immunology 7: 213-226 (1997).

The novel bacterium can also be grown on ASK cells. Growing ASK cells has been described by Sanchez, L in Cytogenet. Cell. Genet. 64:35-38 (1993) and by Devold et al., in Dis. Aquatic Org. 40: 9-19 (2000).

Example 2

Development of Cod's Syndrome, and Koch Postulates Test

In order to study the development of the disease, the onset of clinical signs of the novel bacteria was tested for both deliberately infected fish and fish cohabiting with other fish.

Bacterial Culture.

The novel bacterium was sub-cultured by spread plating onto Blood agar+cys+glu and incubated at 10° C. for 10 days. Subsequently the bacterial growth from all plates was combined and subsequently resuspended in 10 ml MEME (Minimal Essential Medium Eagle (Sigma)).

Fish

A total of 150 juvenile fish (juvenile cod =15-20 gram) were obtained from a hatchery where the novel bacterium has not been found. A number of fish from the same batch were tested by PCR (primers: FC-F2 (5'-ACAGGTCTTCGGAT-GCTGACG)[SEQ ID NO 8] and FC-R1 (5'-TCACTC-CGTGGTAAACGCC)[SEQ ID NO 9] see below) of the internal organs (spleen and kidney) to confirm the absence of the pathogen. All fish analyzed were shown to be free of the pathogen.

The fish were divided as they came at hand in two equally sized groups of 30 fish (one control and one challenged group) and transferred to a 150 L aquarium equipped with a particle filter and UV.

Challenge

For the preparation of the challenge culture, starting agar plates were used of which 50% of the surface was covered with bacteria, i.e. plates were incubated at 15° C. until about 50% of the surface was filled with clear white colonies. Subsequently, a bacterial suspension was obtained by bringing 10 ml of MEME on the agar plates followed by shaking until a homogenous solution was obtained.

One group of fish (N=30) was injected ip with 0.2 ml of the solution. The control fish received only an injection of MEME. The fish were kept in circulating full seawater 10° C. during the experimental period.

Observations After Challenge.

Dead fish were collected twice daily. From all dead fish, a piece of the internal organs was taken and screened by PCR.

Additionally, biopts of the internal organs of a representative number of fish from both groups were streaked onto Blood agar+cys+glu. Plates were incubated at 10° C. for 20 days and the presence of novel bacterial colonies was observed and subsequently confirmed by PCR and sequencing of the 16S rRNA gene.

Results

Fish showing the typical disease signs, i.e. loss of appetite, reduced swimming capacity and dark pigmentation, were seen in the challenged group but not in the control group from day 5 after challenge onwards.

Mortality started on day 5 after challenge in the challenged fish and continued over the following 15 days after which all fish were dead. All dead fish were sampled and analyzed and the typical bacterium according to the invention was isolates on agar or detected in tissues by PCR.

No mortality was observed in the control group during the experimental period. None of the fish sampled in the control group were positive for *Francisella* nsp.

The internal organs of a representative number of fish from both groups were plated onto a suitable medium. The novel bacterium according to the invention was successfully re-isolated from 11 sampled challenged fish, but could not be isolated from any of the control fish.

All fish that died were demonstrated positive for the presence of *Francisella* nsp. after PCR targeting the 16S rRNA gene. The PCR products were sequenced to confirm that the products were identical to the segment of the 16S rRNA gene from *Francisella* nsp.

Fulfilling Koch's Postulates

Koch's postulates are defined as:

1) The same organism must be isolated/demonstrated in all cases showing the same disease signs.
2) The suspected pathogenic organism must be isolated as pure and dominant colony type from the animals showing the disease signs.
3) When the suspected pathogenic organism is administered to healthy susceptible animals they should develop the same disease while showing the typical signs of the disease.
4) The same pathogenic organism must again be re-isolated from the challenged animals as a pure and dominant colony type.

The same organism was found in all cases of the disease. All fish showed the same disease signs, i.e. loss of appetite, reduced swimming capacity and dark pigmentation. The same organism was demonstrated and can be recognized and distinguished from other known pathogens by its appearance: mainly intra-cellular, by its typical morphology, and by its 16S rRNA sequence. Bacteria grown on agar show similar characteristics as the isolate used in the challenge.

Ten days after challenge healthy cod juveniles were added to the tank containing the challenged fish. All fish exposed to the co-habitant challenge developed the typical disease signs as observed in the fish that received the intraperiotoneal challenge. Moreover the challenge organism could be re-isolated from the co-habitant challenged fish as pure and dominant colony type. The bacteria were identified by PCR and sequencing and shown to be the bacteria according to the invention. Thus, Koch's Postulates are fulfilled, and consequently the relation between the disease and the novel bacterium according to the invention as the causative agent has been proven.

Example 3

Further Challenge Experiments in Both Cod and Salmon

Challenge experiments were done on Atlantic salmon having an average weight of 40-50 g in fresh water and on Atlantic cod having an average weight of 20-30 g in seawater (3.5%) tanks at a water temperature of 12° C. The same batch of challenge inocula was used for both species. 20 fish were present in each group at the start of the experiment, i.e., 20 cod were injected intraperitoneally with SHK grown bacteria and only supernatant was injected (no cells), 20 were injected intraperitoneally with bacteria harvested from blood agar plates with additional cystein and resuspended in MEM (approx $10^9$-$10^{10}$ cells/ml->$10^8$-$10^9$ cells per fish). Additionally 20 non treated fish were added as cohabitants to investigate horizontal transmission. The experiments were terminated 19 days post challenge. FIGS. 6 and 7 show the time to onset of mortality and the cumulative mortality over time for Atlantic cod and Atlantic salmon respectively.

Example 4

Transfer of Infection Between Cohabitant Fish

In the examples above it has been demonstrated that intraperitoneal challenge with the bacterium according to the invention can cause Cod's syndrome.

In this experiment it was checked if in fish that are cohabiting the same aquarium, the disease is naturally transferred from diseased fish to healthy fish.

Therefore the following experiment was done:

30 Atlantic cod (average weight 20 g) were injected intraperitoneally (0.1 ml) with homogenized spleen from Atlantic cod showing classical sympthoms of infection received from the field, resuspended in MEM medium. As controls, 30 cod were injected intraperitoneally (0.1 ml) with MEM medium. The fish were kept in separated sea water tanks at 12° C. During the experimental period 15 non treated cohabitant cod were introduced to each tank. The trial was terminated after 5 month and only 11 fish in the i.p. injected group were alive. With respect to the cohabitants, 8 fish were alive at the point of termination. All survivors were subjected to autopsy following termination and this revealed classical sympthoms (white nodules on internal organs) similar to what was observed for the cod from outbreak in the field used to make the homogenate used for challenge.

It thus turned out that healthy non-infected cod swimming in the same aquarium as infected cod, became infected as could be expected for a contagious disease. These cod showed the same clinical signs seen in naturally infected cod.

Example 5

Identification and Histology

Appearance of the Bacteria when Grown on Blood+glu+cys Agar Plates.

Macroscopically, the bacteria, when grown on blood+cys+glu agar have a shiny and practically white appearance.

Electron Microscopy

FIG. 2 shows a transmission electron microscopy of the novel bacterium. A standard method for transmission electron microscopy was used (Karnovsky fixative, dehydration, embedding in EPON, sectioning and microscopy).

As can be seen from this picture, the bacteria are indeed very pleiomorphic in appearance.

Light Microscopy.

FIG. 3 shows a histological section through the spleen tissue of chronic infected Atlantic salmon. The arrows indicate the bacteria according to the invention.

FIG. 4 shows a macroscopic picture of the spleen of an infected cod. The specific white nodules can clearly be seen.

In FIG. 5, bacteria can be seen growing in SHK-1 cells.

The invention claimed is:

1. An isolated rod-shaped pleiomorphic non-motile Gram-negative bacterium causing Cod's Syndrome in fish, wherein a 16S rRNA gene in said bacteria comprises the nucleic acid sequence of SEQ ID NO: 1.

2. The isolated rod-shaped pleiomorphic non-motile Gram-negative bacteria according to claim 1, wherein said bacteria is in a live attenuated form.

3. The isolated rod-shaped pleiomorphic non-motile Gram-negative bacterium according to claim 1, wherein said bacteria is in an inactivated form.

4. The isolated rod-shaped pleiomorphic non-motile Gram-negative bacterium according to claim 1, comprising the nucleotide sequence as depicted in SEQ ID NO 3.

5. A microbiological culture comprising isolated bacterium according to claim 1.

6. A vaccine for combating Cod's Syndrome in fish, wherein said vaccine comprises bacterium according to claim 1 and a pharmaceutically acceptable carrier.

7. The vaccine according to claim 6, wherein said vaccine comprises at least one other microorganism or virus that is pathogenic to fish, or one other antigen or genetic material encoding said other antigen, wherein said other antigen or genetic material is derived from a virus or microorganism pathogenic to fish.

8. The vaccine according to claim 7, wherein said virus or microorganism pathogenic to fish is selected from the group consisting of the fish pathogens *Vibrio anguillarum, Aeromonas salmonicidae, Vibrio salmonicidae, Moritella viscose, Vibrio ordalii, Flavobacterium* sp., *Flexibacter* sp., *Streptococcus* sp., *Lactococcus garviae, Edwardsiella tarda, E. icta-*

*luri, Piscirickettsia salmonis*, SPD virus, SD virus, VNN virus, IPN virus and iridoviruses.

9. The vaccine according to claim 6, wherein said vaccine comprises an adjuvant.

10. A diagnostic test kit for the detection of antibodies reactive with bacterium according to claim 1, wherein said test kit comprises bacterium according to claim 1.

* * * * *